(12) United States Patent
Ofori et al.

(10) Patent No.: US 6,521,777 B2
(45) Date of Patent: Feb. 18, 2003

(54) PROCESS FOR THE PRODUCTION OF DIARYL CARBONATES

(75) Inventors: John Yaw Ofori, Niskayuna, NY (US); Eric James Pressman, East Greenbush, NY (US); Kirill Vladimirovich Shalyaev, Clifton Park, NY (US); Eric Douglas Williams, Schenectady, NY (US); Richard Anthony Battista, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/961,745

(22) Filed: Sep. 24, 2001

(65) Prior Publication Data

US 2002/0077496 A1 Jun. 20, 2002

Related U.S. Application Data

(63) Continuation-in-part of application No. 09/736,751, filed on Dec. 14, 2000, now abandoned.

(51) Int. Cl.$^7$ .............................................. C07C 69/96
(52) U.S. Cl. ...................................................... 558/274
(58) Field of Search ........................................ 558/274

(56) References Cited

U.S. PATENT DOCUMENTS

| | | |
|---|---|---|
| 4,187,242 A | 2/1980 | Chalk |
| 4,201,721 A | 5/1980 | Hallgren |
| 5,132,447 A | 7/1992 | King |
| 5,142,087 A | 8/1992 | Joerg et al. |
| 5,210,269 A | 5/1993 | Di Muzio et al. |
| 5,231,210 A | 7/1993 | Joyce et al. |
| 5,239,106 A | 8/1993 | Shafer |
| 5,284,964 A | 2/1994 | Pressman et al. |
| 5,306,804 A | 4/1994 | Liehr et al. |
| 5,373,083 A | 12/1994 | King et al. |
| 5,380,907 A | 1/1995 | Mizukami et al. |
| 5,399,734 A | 3/1995 | King, Jr. et al. |
| 5,498,742 A | 3/1996 | Buysch et al. |
| 5,498,789 A | 3/1996 | Takagi et al. |
| 5,502,232 A | 3/1996 | Buysch et al. |
| 5,543,547 A | 8/1996 | Iwane et al. |
| 5,563,293 A | 10/1996 | Hindmarsh et al. |
| 5,625,091 A | 4/1997 | Buysch et al. |
| 5,726,340 A | 3/1998 | Takagi et al. |
| 5,760,272 A | 6/1998 | Pressman et al. |
| 5,821,377 A | 10/1998 | Buysch et al. |
| 5,856,554 A | 1/1999 | Buysch et al. |
| 5,917,078 A | 6/1999 | Battista et al. |
| 6,114,564 A | 9/2000 | Pressman et al. |
| 6,172,254 B1 | 1/2001 | Pressman et al. |
| 6,180,812 B1 | 1/2001 | Johnson et al. |
| 6,197,991 B1 | 3/2001 | Spivack et al. |

FOREIGN PATENT DOCUMENTS

| | | |
|---|---|---|
| EP | 071286 | 2/1983 |
| EP | 0 350 700 | 1/1990 |
| EP | 736325 | 3/1996 |
| GB | 1102566 | 2/1968 |
| JP | 92-257546 | 9/1992 |
| JP | 92-261142 | 9/1992 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |
| JP | 98-10158221 | 6/1998 |
| JP | 98-10316627 | 12/1998 |
| WO | WO 00/37413 | 6/2000 |
| WO | WO 00/37419 | 6/2000 |
| WO | WO 00/66534 | 11/2000 |
| WO | WO 00/66536 | 11/2000 |

OTHER PUBLICATIONS

PCT Search Report for International Application No. PCT/US/01/43496.

*Primary Examiner*—Taofiq Solola
(74) *Attorney, Agent, or Firm*—S. Bruce Brown; Noreen C. Johnson (57) ABSTRACT

A process for catalytic production of diaryl carbonates by oxidative carbonylation of aromatic hydroxy compounds with carbon monoxide and oxygen achieves water removal during reaction by a process comprising the steps of: removing a liquid stream from an oxidative carbonylation reaction mixture in a reaction vessel and transferring the stream to a disengagement vessel, transferring a stream from the disengagement vessel to a flash vessel and subjecting the liquid stream to reduced pressure, and returning at least a portion of dried liquid stream to the reaction vessel. Typical catalyst systems for oxidative carbonylation contain (A) at least one Group 8, 9, or 10 metal having an atomic number of at least 44 or a compound thereof; (B) at least one guanidinium salt or onium salt; (C) at least one metal co-catalyst; and (D) at least one base.

105 Claims, 2 Drawing Sheets

PROCESS FOR THE PRODUCTION OF DIARYL CARBONATES

CROSS-REFERENCE TO RELATED APPLICATIONS

This application is a continuation-in-part of copending U.S. application Ser. No. 09/736,751, filed Dec. 14, 2000 now abandoned, which is incorporated herein by reference.

BACKGROUND OF THE INVENTION

The present invention is related to an improved process for the removal of undesirable water from a chemical reaction for producing products in which water is deleterious to the process and/or products produced therefrom. In particular, the products are carbonate esters, and more particularly diarylcarbonates, prepared by the oxidative carbonylation of aromatic hydroxy compounds, such as by the reaction with carbon monoxide and oxygen in the presence of a catalyst generally containing a metal of group 8, 9, or 10 of the Periodic Table of Elements and a co-catalyst. The process of this invention allows continuous removal of water without depressurization of a reaction vessel.

Water removal in the oxidative carbonylation of aromatic hydroxy compounds to make diarylcarbonates is a desirable process since it enhances the productivity of the reaction and thus reduces reactor cost per unit mass of product. This is demonstrated by the improvement obtained when molecular sieves are used for water removal in reactions to make diphenyl carbonate (DPC), as described in U.S. Pat. No. 5,399,734 and in co-pending application Ser. No. 09/224, 162, filed Dec. 31, 1999.

U.S. Pat. No. 5,625,091 describes water removal from oxidative carbonylation reaction mixtures under reduced pressure. U.S. Pat. No. 5,498,472 describes water removal from oxidative carbonylation reaction mixtures by excess process gas flow at relatively low pressures. Both of these latter two methods are specific to reaction mixtures containing a specified catalyst type which employs a quaternary salt and a base. An inert stripping agent has also been used for removing water from reaction mixtures for oxidative carbonylation of aromatic hydroxy compounds as described in U.S. Pat. No. 5,917,078.

The problem to be solved is to develop a reaction process which removes water from an oxidative carbonylation reaction mixture continuously with no need to depressurize the reaction vessel or vessels, and without the requirement of using an entrained gas process or water absorbing agent. In this manner the water content inside the reactor or reactors may be kept below a prescribed value, in a manner which retains the activity of the catalyst system and minimizes the utilities requirements.

BRIEF SUMMARY OF THE INVENTION

After careful study the present inventors have discovered methods for removing water of reaction in an integrated process for oxidative carbonylation of aromatic hydroxy compounds which avoids the problems of earlier methods. Thus, in one of its embodiments the present invention is a method for preparing a diaryl carbonate which comprises contacting at least one aromatic hydroxy compound with oxygen and carbon monoxide in the presence of an amount effective for carbonylation of a catalyst composition comprising the following and any reaction products thereof:
(A) at least one Group 8, 9, or 10 metal having an atomic number of at least 44 or a compound thereof;
(B) at least one guanidinium salt or onium salt;
(C) at least one metal co-catalyst; and
(D) at least one base,
wherein reaction water is removed by a process comprising the steps of:
(i) removing a liquid stream from an agitated oxidative carbonylation reaction mixture by transferring the stream from a reaction vessel to a first disengagement vessel which is not agitated;
(ii) optionally, reducing the temperature of the liquid stream;
(iii) transferring a liquid stream from the first disengagement vessel to a flash vessel wherein the liquid stream is subjected to reduced pressure, whereby a majority of the water is removed;
(iv) returning at least a portion of a dried liquid stream to the reaction vessel; and
(v) optionally adding at least one of make-up aromatic hydroxy compound or other volatile constituent or catalyst component to the reaction vessel or to the dried liquid stream before return to the reaction vessel,
wherein at least a portion of diaryl carbonate is recovered from a liquid stream either before or after water removal.

DETAILED DESCRIPTION OF THE INVENTION

For the sake of brevity, the constituents of the catalyst system are defined as "components" irrespective of whether a reaction between said constituents occurs before or during the carbonylation reaction. Thus, the catalyst system may include said components and any reaction products thereof. The terms "reactor" and reaction vessel" are used interchangeably.

Unless otherwise noted, the term "effective amount", as used herein, includes that amount of a substance capable of either increasing (directly or indirectly) the yield of the carbonylation product or increasing selectivity toward an aromatic carbonate. Optimum amounts of a given reactant can vary based on reaction conditions and the identity of other constituents, yet can be readily determined in light of the discrete circumstances of a given application.

Any aromatic hydroxy compound convertible to a carbonate ester may be employed in the present invention. Suitable aromatic hydroxy compounds include monocyclic, polycyclic or fused polycyclic aromatic monohydroxy or polyhydroxy compounds having from 6 to 30, and preferably from 6 to 15 carbon atoms. Illustrative examples include mono- and poly-hydroxy compounds such as phenol, alkylphenols, o-, m- or p-cresol, o-, m- or p-chlorophenol, o-, m- or p-ethylphenol, o-, m- or p-propylphenol, o-, m- or p-methoxyphenol, methyl salicylate, 2,6-dimethylphenol, 2,4-dimethylphenol, 3,4-dimethylphenol, 1-naphthol and 2-naphthol, xylenol, resorcinol, hydroquinone, catechol, cumenol, the various isomers of dihydroxynaphthalene, bis(4-hydroxyphenyl) propane-2,2,α,α'-bis(4-hydroxyphenyl)-p-diisopropylbenzene, and bisphenol A. Aromatic monohydroxy compounds are particularly preferred with phenol being the most preferred. In the case of substituents on the aromatic hydroxy compound, the substituents are generally 1 or 2 substituents and are preferably from C-1 to C-4 alkyl, C-1 to C-4 alkoxy, fluorine, chlorine or bromine.

When an aromatic hydroxy compound as a raw material is used as a reaction solvent, then another solvent need not be used. However, the reaction mixture may also optionally contain at least one inert solvent, that is a solvent whose presence does not improve the yield of or selectivity toward the aromatic carbonate. Illustrative inert solvents include, but are not limited to, hexane, heptane, cyclohexane, methylene chloride, or chloroform.

Other reagents in the method of this invention are oxygen and carbon monoxide, which react with the aromatic hydroxy compound to form the desired diaryl carbonate. The carbon monoxide may be high-purity carbon monoxide or carbon monoxide diluted with another gas which has no negative effects on the reaction, such as nitrogen, noble gases, argon, or carbon dioxide. The oxygen used in the present invention may be high purity oxygen, air, or oxygen diluted with any other gas which has no negative effects on the reaction, such as nitrogen, noble gases, argon, or carbon dioxide. The concentration of inert gas in the reaction gas may amount to 0 to about 60 volume %, preferably 0 to about 20, and more preferably 0 to about 5 volume %. The concentration of 0 volume % represents the special case of the preferred state which is free of inert gas.

The composition of the reaction gases carbon monoxide and oxygen can be varied in broad concentration ranges. Preferably a carbon monoxide:oxygen molar ratio (normalized on carbon monoxide) of 1:(0.001–1.0) is employed, more preferably 1:(0.01–0.5) and still more preferably 1:(0.02–0.3). The reaction gases are not subject to special purity requirements but care must be taken to ensure that no catalyst poisons such as sulfur or compounds thereof are introduced. In the preferred embodiment of the process according to the invention, pure carbon monoxide and pure oxygen are used. In a further preferred embodiment of the process according to the invention, carbon monoxide and oxygen may be added independently of each other. The oxygen addition, in this case, can take place, if desired, together with inert gas. When a reactor cascade is used instead of an individual reactor, the separate oxygen addition preferably proceeds in such a way that the optimal oxygen concentration is ensured in each of the reactors.

The reaction gas, comprising carbon monoxide, oxygen and, optionally, an inert gas, may be typically introduced at a rate of about 1 to about 100,000 liters (S.T.P.) per liter of reaction solution, preferably about 5 to about 50,000 liters (S.T.P.) per liter of reaction solution and particularly preferably about 10 to about 10,000 liters (S.T.P.) per liter of reaction solution.

The catalyst employed herein contains at least one Group 8, 9, or 10 metal having an atomic number of at least 44 or a compound thereof, preferably palladium. The palladium material useful as a catalyst (sometimes referred to hereinafter as palladium source) can be in elemental form or it can be employed as a palladium compound. The palladium material can be employed in a form that is substantially soluble in the reaction media or in a form which is substantially insoluble in the reaction media, such as a supported- or polymer-bound palladium species. Thus, useful palladium materials include elemental palladium-containing entities such as palladium black, palladium deposited on carbon, palladium deposited on alumina and palladium deposited on silica; palladium compounds such as palladium chloride, palladium bromide, palladium iodide, palladium sulfate, palladium nitrate, palladium carboxylates, palladium acetate and palladium 2,4-pentanedionate; and palladium-containing complexes involving such compounds as carbon monoxide, amines, nitrites, phosphines and olefins. As used herein, the term "complexes" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes. Preferred in many instances are palladium (II) salts of organic acids, most often $C_{2-6}$ aliphatic carboxylic acids, and palladium (II) salts of β-diketones. Palladium (II) acetate and palladium (II) 2,4-pentanedionate (also know as palladium (II) acetylacetonate) are generally most preferred. Mixtures of palladium materials are also contemplated.

The quantity of the at least one Group 8, 9, or 10 metal catalyst is not particularly limited in the process of the present invention. An effective amount of the at least one Group 8, 9, or 10 metal catalyst, particularly palladium, is, for example, an amount sufficient to provide about 1 gram-atom of metal per 800–1,000,000, more preferably per 4000–1,000,000, still more preferably per 40,000–200,000, and more preferably per 65,000–100,000 moles of aromatic hydroxy compound fed to the reactor. Aromatic hydroxy compound fed to the reactor includes that aromatic hydroxy compound fed directly to the reactor and that aromatic hydroxy compound recycled to a reactor or added as make-up aromatic hydroxy compound, all of which may include catalyst.

The catalyst employed herein also contains at least one salt with anion selected from tetrafluoroborates, hexafluorophosphates and halides. The cation portion of the salt can be at least one guanidinium salt or onium salt, including ammonium, phosphonium, or sulfonium salts that are substituted with organic residues. Illustrative examples of guanidinium salts include, but are not limited to, hexasubstituted guanidinium halides, such as hexaalkyl guanidinium halides, hexaaryl guanidinium halides, and hexasubstituted guanidinium halides containing mixtures of alkyl and aryl substituents each substituent group independently having a carbon number of 1 to 22; for example hexaalkylguanidinium chlorides or bromides. In one embodiment of the invention hexaethylguanidinium bromide is preferred. Illustrative examples of onium salts include, but are not limited to, tetraalkylammonium or tetraalkylphosphonium halides, tetrafluoroborates, or hexafluorophosphates. In preferred embodiments the salts are halides such as the chlorides and bromides, particularly the bromides. Organic residues on the onium salts are typically include $C_{6-10}$ aryl, $C_{7-12}$ aralkyl, or $C_{1-20}$ alkyl, or combinations thereof. Preferred onium salts are alkyl ammonium halides containing primary and/or secondary alkyl groups containing about 1–8 carbon atoms. Tetraethylammonium bromide is particularly preferred.

Mixtures of the aforementioned salts are also suitable for use in the invention. The at least one salt is typically present in the reaction mixture in an amount of about 1–2000 moles, preferably about 2–1500 moles, and more preferably about 5–1000 moles per gram-atom of Group 8, 9, or 10 metal catalyst.

There also can be used in combination with the Group 8, 9, or 10 metal catalyst and catalyst system at least one quinone and aromatic diol formed by the reduction of said quinone or a mixture thereof. 1,4-benzoquinone and hydroquinone are preferred. In addition, compounds such as 1,2-quinone and catechol, anthraquinone, 9,10-dihydroxyanthracene, and phenanthrenequinone also can be used. When present, the at least one quinone and aromatic diol formed by the reduction of said quinone or a mixture thereof may be present in an amount of about 10–60, and preferably about 25–40 moles of quinone and/or reduction product thereof per gramatom of Group 8, 9, or 10 metal catalyst.

In addition to the at least one Group 8, 9, or 10 metal catalyst having an atomic number of at least 44 there is present in the reaction mixtures of the invention an effective amount of at least one metal co-catalyst (component C) containing a metal different from the at least one Group 8, 9, or 10 metal. Suitable metal co-catalysts include all those known in the art which promote formation of carbonate ester from aromatic hydroxy compound under reactive conditions in the presence of the at least one Group 8, 9, or 10 metal catalyst having an atomic number of at least 44. Metal co-catalysts include elemental metals, metal compounds, and precursors thereof which may form catalytically active metal species under the reaction conditions, it being possible for use to be made of the metal in various degrees of oxidation. Metal co-catalysts may be initially soluble in the reaction mixture or initially insoluble as in supported- or polymer-bound metal co-catalyst species. Alternatively, metal co-catalysts may be initially insoluble in the reaction mixture and form soluble metal co-catalyst species during the course of the reaction. Illustrative metals in the co-catalysts include cerium, titanium, cobalt, copper, zinc, manganese, and lead, which may be used singly or in combination. Preferred metal co-catalysts comprise manganese or cobalt. More preferred are compounds of lead, particularly when used alone or in combination with at least one of titanium, copper, or cerium.

The at least one metal co-catalyst can be introduced to the carbonylation reaction in various forms, including salts and complexes, such as tetradentate, pentadentate, hexadentate, or octadentate complexes. Illustrative forms may include oxides, halides, carboxylates (for example of carboxylic acids containing from 2–6 carbon atoms), diketones (including beta-diketones), nitrates, complexes containing carbon monoxide, olefins, amines, phosphines and halides, and the like. Suitable beta-diketones include those known in the art as ligands for the metal co-catalysts of the present invention. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). A metal co-catalyst may be used in its elemental form if sufficient reactive surface area can be provided.

One preferred class of metal co-catalysts comprises at least one manganese source (sometimes referred to hereinafter as manganese compound). Examples of manganese compounds include manganese halides, manganese chloride, manganese bromide, manganese nitrate, manganese carboxylates such as manganese (II) acetate, and manganese salts of β-diketones such as manganese (III) 2,4-pentanedionate and manganese (II) 2,4-pentanedionate (manganese (II) acetylacetonate). Mixtures of manganese compounds may also be employed. The preferred manganese compounds are manganese 2,4-pentanedionates.

One preferred class of metal co-catalysts comprises at least one cobalt source (sometimes referred to hereinafter as cobalt compound). Examples of cobalt compounds include cobalt halides, cobalt chloride, cobalt bromide, cobalt nitrate, cobalt carboxylates such as cobalt (II) acetate and cobalt (II) 2-ethylhexanoate; and cobalt salts of β-diketones such as cobalt (III) 2,4-pentanedionate and cobalt (II) 2,4-pentanedionate (cobalt (II) acetylacetonate). Mixtures of cobalt compounds may also be employed. The preferred cobalt compounds are cobalt 2,4-pentanedionates.

Still another preferred class of metal co-catalysts comprises at least one lead source (sometimes referred to hereinafter as lead compound). A lead compound is preferably soluble in a liquid phase under the reaction conditions. Examples of such lead compounds include, but are not limited to, lead oxides, for example PbO, $Pb_3O_4$, and $PbO_2$; lead carboxylates, for example lead (II) acetate and lead (II) propionate; inorganic lead salts such as lead (II) nitrate and lead (II) sulfate; alkoxy and aryloxy lead compounds such as lead (II) methoxide, and lead (II) phenoxide; lead complexes such as lead (II) acetylacetonate and phthalocyanine lead, and organolead compounds (that is lead compounds having at least one lead-carbon bond) such as tetraethyl lead. Of these compounds, lead oxides and lead compounds represented by the formula Pb(OR)2 wherein R is an aryl group having a carbon number from 6 to 10 are preferred. Mixtures of the aforementioned lead compounds are also contemplated.

Examples of cerium sources (sometimes referred to hereinafter as cerium compounds) include cerium carboxylates such as cerium acetate, and cerium salts of β-diketones such as cerium (III) 2,4-pentanedionate (cerium (III) acetylacetonate). Mixtures of cerium compounds may also be employed. The preferred cerium compounds are cerium 2,4-pentanedionates.

Examples of titanium sources (sometimes referred to hereinafter as titanium compounds) are inorganic titanium salts such as titanium (IV) bromide, titanium (IV) chloride; titanium alkoxides and aryloxides such as titanium (IV) methoxide, titanium (IV) ethoxide, titanium (IV) isopropoxide, titanium (IV) 2-ethylhexoxide, titanium (IV) butoxide, titanium (IV) 2-ethyl-1,3-hexanediolate, titanium (IV) (triethanolaminato)-isopropoxide and titanium (IV) phenoxide; and titanium salts of β-diketones or β-ketoesters such as titanium (IV) diisopropoxide bis(acetylacetonate), titanium (IV) bis(ethyl acetoacetato) diisopropoxide, titanium (IV) oxide bis(2,4-pentanedionate) (or titanium (IV) oxide acetylacetonate). Mixtures of titanium compounds may also be employed. The preferred titanium compounds are titanium (IV) alkoxides and aryloxides such as titanium (IV) butoxide and titanium (IV) phenoxide; and salts of β-diketones or β-ketoesters such as titanium (IV) oxide acetylacetonate and titanium (IV) bis(ethyl acetoacetato) diisopropoxide.

Examples of copper sources (sometimes referred to hereinafter as copper compounds) are inorganic cupric or cuprous salts or copper complexes. Illustrative examples include, but are not limited to, copper (I) chloride, copper (I) bromide, copper (I) iodide; copper (II) chloride, copper (II) bromide, copper (II) iodide; copper carboxylates such as copper acetate, copper gluconate, and copper (II) 2-ethylhexanoate; copper (II) hydroxide, copper alkoxides and aryloxides; copper nitrate; and copper salts of β-diketones such as copper (II) bis(2,4-pentanedionate) (or copper (II) acetylacetonate). Mixtures of copper compounds may also be employed. The preferred copper compounds are 2,4-pentanedionates. Another preferred class of metal co-catalysts comprises a combination of at least one titanium source and at least one copper source.

In addition to those illustrated above, one or more additional metal co-catalysts may be used in the carbonylation catalyst system, provided any additional metal co-catalyst does not deactivate (i.e. "poison") the original metal co-catalyst or cocatalyst combination, such that it loses its effectiveness. A non-exclusive listing of additional metal co-catalysts includes iron, ytterbium, zinc, europium, bismuth, nickel, iridium, rhodium, ruthenium, chromium, and yttrium.

The at least one metal co-catalyst is included in the carbonylation catalyst system in effective amounts. In this context an "effective amount" is an amount of metal co-catalyst (or combination of metal co-catalysts) that increases the number of moles of aromatic carbonate produced per mole of Group 8, 9, or 10 metal catalyst utilized; increases the number of moles of aromatic carbonate produced per mole of salt utilized; or increases selectivity toward aromatic carbonate production beyond that obtained in the absence of the metal co-catalyst (or combination of metal co-catalysts). Optimum amounts of an metal co-catalyst in a given application will depend on various factors, such as the identity of reactants and reaction conditions. Typically, the at least one metal co-catalyst component C is present in the amount of about 0.1–200 gram-atoms, preferably about 1–150 gram-atoms, and more preferably about 2–100 gram-atoms of total metals in component C per gram-atom of the Group 8, 9, or 10 metal of component A. Total metals in component C means the combination of all the metals in component C which may comprise one metal or more than one metal. In embodiments wherein the metal co-catalyst comprises at least one copper compound and at least one lead compound, then the mole ratio of copper to lead is about 2–10 moles copper to about 100 moles lead. In other embodiments when palladium, titanium, and copper are included in the reaction, the molar ratio of titanium relative to palladium at the initiation of the reaction is in one embodiment in a range of between about 0.1 and about 150, and the molar ratio of copper relative to palladium is at the initiation of the reaction is in one embodiment in a range of between about 0.1 and about 15. In other embodiments the mole ratio of copper to titanium is about 5–20 moles copper to about 2–30 moles titanium.

At least one base (component D) is present in the reaction mixture. Any effective bases or mixtures thereof, whether organic or inorganic may be used in the process of the invention. In preferred embodiments a base is used which is capable of generating the conjugate base of an aromatic hydroxy compound and not interfering with the function of any catalyst component. Illustrative examples of inorganic bases include, but are not limited to, alkali metal hydroxides and alkali metal carbonates, alkali metal carboxylates or other salts of weak acids or alkali metal salts of aromatic hydroxy compounds, for example alkali metal phenoxides. Obviously, the hydrates of alkali metal phenoxides can also be used in the process. An example of such a hydrate which may be mentioned is sodium phenoxide trihydrate. In general the use of hydrates and the concomitant addition of water to the reaction mixture may lead, inter alia, to poorer conversion rates and decomposition of carbonates formed. Illustrative examples of organic bases include, but are not limited to, onium hydroxides, onium phenoxides, ammonium hydroxides, ammonium phenoxides, phosphonium hydroxides, phosphonium phenoxides, sulfonium hydroxides, sulfonium phenoxides, guanidinium hydroxides, guanidinium phenoxides, tertiary amines which bear as organic radicals $C_6$–$C_{10}$ aryl, $C_6$–$C_{12}$ aralkyl and/or $C_1$–$C_{20}$-alkyl or represent pyridine bases or hydrogenated pyridine bases; for example dimethylbutylamine, triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxy compound, particularly preferably an alkali metal salt of the aromatic hydroxy compound which is also to be converted to the organic carbonate. These alkali metal salts can be lithium salts, sodium salts, potassium salts, rubidium salts or cesium salts. Lithium phenoxide, sodium phenoxide and potassium phenoxide are preferably used; sodium phenoxide is particularly preferred.

A base may be added as a pure compound or as a precursor compound, such as addition of an alkali metal-comprising base as a precursor for an alkali metal salt of the aromatic hydroxy compound which is also to be converted to the organic carbonate. Illustrative alkali metal-comprising bases include, but are not limited to, sodium hydroxide, and sodium salts of weak acids such as sodium carboxylates, sodium acetate, and sodium acetylacetonate. A base may be added to the reaction mixture in any convenient form, such as in solid form or as a liquid or a melt, either in neat form or in a solution. In a further embodiment of the invention, the base is added to the reaction mixture as a solution which contains about 0.1 to about 80% by weight, preferably about 0.5 to about 65% by weight, particularly preferably about 1 to about 50% by weight of the base. The solvents which may optionally be used here are both alcohols or phenols, such as the phenol to be reacted, and inert solvents. Examples of solvents which may be mentioned are dimethylacetamide, N-methylpyrrolidinone, dioxane, t-butanol, cumyl alcohol, isoamyl alcohol, tetramethylurea, diethylene glycol, halogenated hydrocarbons (e.g. chlorobenzene or dichlorobenzene) and ethers, such as tetraethylene glycol dimethyl ether. The solvents may be used alone or in any combination with each other.

A base is added in an amount independent of the stoichiometry. The ratio of base to Group 8, 9, or 10 metal having an atomic number of at least 44 is preferably chosen in such a way that at least one base is present in an amount in a range of about 0.1 to about 2500, preferably about 5 to about 1500, more preferably about 50 to 1000, and still more preferably about 100 to 400 molar equivalents of base based on component A.

The oxidative carbonylation reaction can be carried out in a batch reactor, or a semi-continuous, or continuous reactor system comprising one or more reaction vessels. Reaction vessels suitable for use in the process according to the invention with either homogeneous or heterogeneous catalysts include stirrer vessels, autoclaves and bubble columns, it being possible for these to be employed as individual reactors or as a cascade. In a cascade 2 to 15, preferably 2 to 10, and particularly preferably 2 to 5, reactors may be connected in series.

The method of the invention is preferably conducted in at least one reaction vessel in which the aromatic hydroxy compound, catalyst system, and any other components are charged to a reactor, pressurized under carbon monoxide and oxygen, and heated. The reaction pressure is most often in a range of about 0.1–51 megapascals, preferably about 0.3–25 megapascals, more preferably about 1.0–17 megapascals and still more preferably about 1.1–15 megapascals. Gas is usually supplied in proportions of about 1–50 mole percent oxygen with the balance being carbon monoxide. Additional gases may be present in amounts that do not deleteriously affect the carbonylation reaction. The gases may be introduced separately or as a mixture. Reaction temperatures in the range of about 30–210° C. and preferably about 50–160° C. are typical, with temperatures in the range of about 80–125° C. being more preferred. Agitation of the reaction mixture in at least one reaction vessel is preferably employed to aid the reaction. Agitation may be performed by any known method, including at least one of stirring or gas sparging.

In order for the reaction to be as rapid as possible, it is preferred to substantially maintain the total gas pressure and partial pressure of carbon monoxide and oxygen until a desired conversion level of aromatic hydroxy compound is achieved, as described, for example, in U.S. Pat. No. 5,399,734, which is incorporated herein by reference.

The diaryl carbonates produced by this method may be recovered at any convenient point in the process loop and isolated by conventional techniques. It is often preferred to form and thermally crack an adduct of the diaryl carbonate with the hydroxy aromatic compound, as is described in U.S. Pat. Nos. 5,239,106 and 5,312,955, which are incorporated herein by reference.

Figure 1:
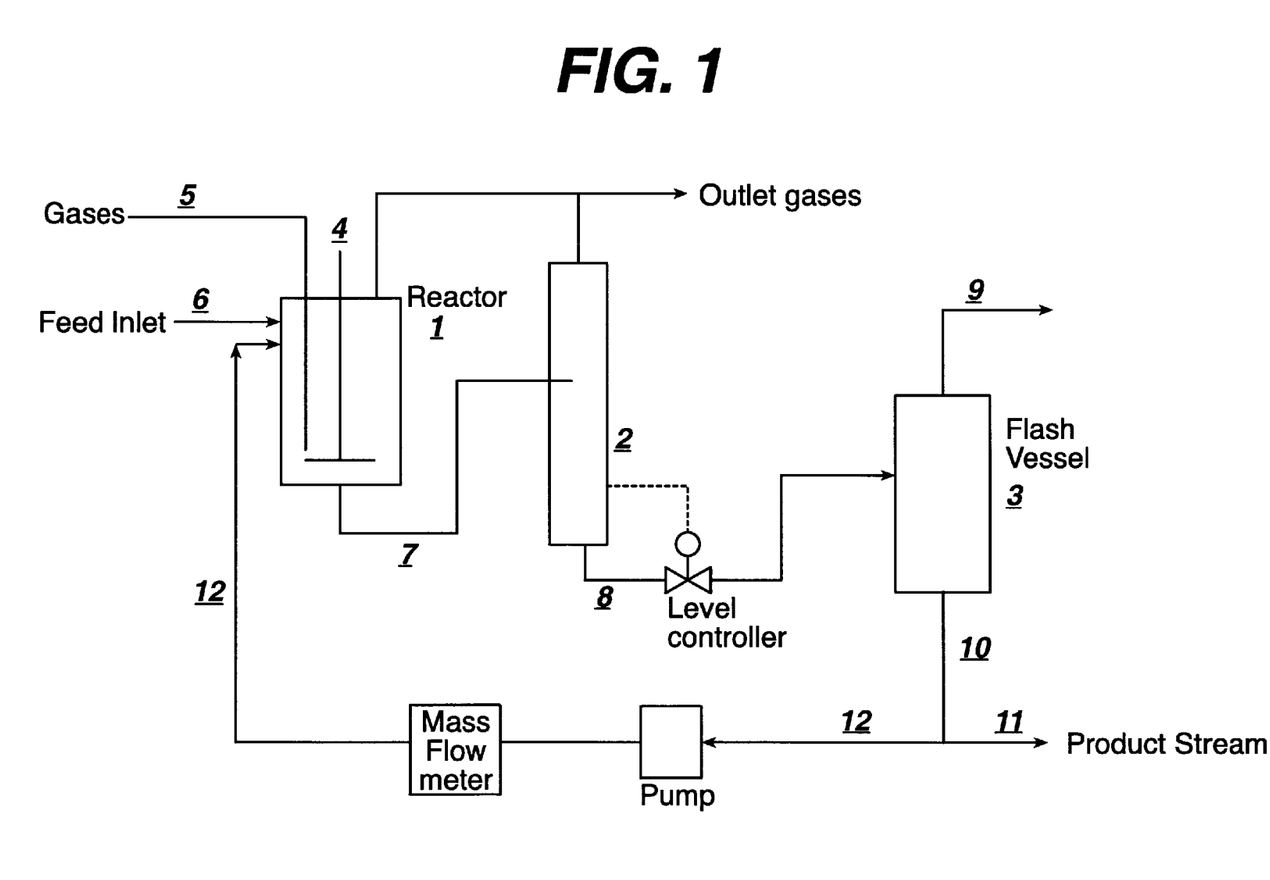
FIG. 1 is a flow diagram for a process which removes water.

Water removal in an integrated process for oxidative carbonylation of aromatic hydroxy compounds may be illustrated with reference to the flow diagrams of FIG. 1 and FIG. 2. In FIG. 1 at least one reaction vessel (1) has contents comprising aromatic hydroxy compound and catalyst system under pressure of carbon monoxide and oxygen. The reactor contents may be agitated by known means; in the embodiment in FIG. 1 agitation is illustrated by stirrer (4). Carbon monoxide, oxygen, and optional other gas may be fed to a reactor (1) through one or more gaseous feed inlets; in the embodiment in FIG. 1 a single gaseous feed inlet (5) is illustrated. Catalyst and liquid (for example, aromatic hydroxy compound) may be fed to a reactor (1) via one or more feed inlets; in the embodiment in FIG. 1 a single feed inlet (6) is illustrated. A liquid stream to be dried may be removed from a reaction vessel via an outlet (7) for transfer to a first disengagement vessel (2). The amount of liquid stream withdrawn per hour may amount to about 0.01 to 30 times, preferably about 0.05 to 20 times, and particularly preferably about 0.1 to 10 times, the contents of the reactor.

Removal of a liquid stream may be by any convenient method, preferably by gravity or pump or a combination thereof. As shown in an embodiment in FIG. 1 a liquid stream may be removed from reaction vessel (1) when the liquid level of reaction mixture reaches a level equivalent to the highest level of outlet (7). Thus, in one embodiment as material is continuously pumped into reaction vessel (1) a corresponding flow of material may transfer continuously to disengagement vessel (2) via outlet (7). In alternative embodiments the liquid level in reaction vessel (1) may go temporarily over the highest level of outlet (7) by temporarily closing outlet (7). In yet other alternative embodiments the liquid level in reaction vessel (1) may be temporarily below the highest level of outlet (7) and transfer to disengagement vessel (2) may be performed by pump. The exact mode of operation at a particular time offers beneficial alternatives and may depend on such factors as the degree of conversion of aromatic hydroxy compound to diarylcarbonate under the particular process conditions.

Disengagement vessel (2) is not agitated. Not agitated means that no deliberate means of agitation is employed other than adventitious agitation, such as that which may occur when a liquid stream is transferred to or from disengagement vessel (2). By maintaining the liquid stream in disengagement vessel (2) without agitation, gases which had been entrained by agitation in reaction vessel (1) may escape from the liquid stream.

The liquid stream in disengagement vessel (2) may be at a pressure in a range of between about atmospheric pressure and the pressure in reaction vessel (1). In some embodiments the liquid stream in disengagement vessel (2) may be at a pressure which is lower than that in reaction vessel (1). In one embodiment the liquid stream in disengagement vessel (2) is at essentially the same pressure as the reaction mixture in reaction vessel (1). In another embodiment the liquid stream in disengagement vessel (2) is at essentially the same temperature and pressure as the reaction mixture in reaction vessel (1).

Although the invention is in no way dependent upon mechanism, it is believed that without agitation oxygen dissolved in the liquid steam in disengagement vessel (2) may be consumed through reaction leaving a high concentration of dissolved carbon monoxide. A high concentration of carbon monoxide and also possibly high temperature in the absence of sufficient oxygen may be detrimental to catalyst activity and lifetime depending upon catalyst composition. The catalyst system must be able to withstand the process sequence, particularly the gas disengagement at the reaction temperature and pressure, such that when it is returned to the reactor following removal of water the catalyst activity is maintained or minimally reduced.

Outlet gases (13) from reaction vessel (1) and disengagement vessel (2) are recycled using standard methods. Typically outlet gases are cooled to condense and remove water and other condensable compounds before reuse of gases.

In one embodiment of the water removal process a liquid stream from disengagement vessel (2) is transferred via outlet (8) to at least one flash vessel (3). A flash vessel for evaporation of water may be any type of apparatus known to those skilled in the art for this purpose. For example, a flash vessel may comprise vertical-pipe, horizontal-pipe, slanting-pipe, rotor or thin-layer, centrifugal, worm and falling-film evaporators, tube-bundle evaporators, basket evaporators, evaporators with external return pipe and forced circulation, evaporators with external heating elements and forced circulation and other evaporators known to those skilled in the art. Furthermore, simple distillation and rectifying columns with accompanying heating elements are also suitable; preferably a flash vessel comprises thin-layer and falling-film evaporators and evaporators with forced circulation and heating elements located internally or externally.

Flash vessel (3) may represent a single flash vessel or more than one flash vessel, each with at least one stage. In one embodiment at least one flash vessel has more than one stage, for example two or three stages. The liquid stream from disengagement vessel (2) can be transferred continuously, semi-continuously (for example, periodically), or in a batch which essentially empties all of disengagement vessel (2). If desired, the temperature of the liquid stream portion removed from disengagement vessel (2) may be lowered from the temperature of the initial reaction mixture by cooling disengagement vessel (2) or through heat exchange during transfer from outlet (8), or both. When the temperature is lowered, it is typically lowered to a temperature in a range between about 50° C. and about 90° C.

In flash vessel (3) the liquid stream portion is subjected to a reduced pressure in that the pressure is lower than the pressure in reaction vessel (1). Typically the reduced pressure is in the range of about 0.1–500 kilopascals, preferably about 0.7–53 kilopascals, more preferably about 0.7–40 kilopascals, still more preferably about 0.7–13 kilopascals, and yet still more preferably about 2–7 kilopascals, and a temperature in the range of about 50–160° C. for removal of a majority of the water and varying amounts of aromatic hydroxy compound and any other volatile constituents through outlet (9). Because entrained gases have escaped from the liquid stream in disengagement vessel (2), less aromatic hydroxy compound is entrained and lost from flash vessel (3) when the liquid stream from (8) undergoes pressure drop in flash vessel (3). In the present context majority of water means greater than about 50% by weight, preferably about 50–99% by weight, and more preferably about 50–80% by weight of water in the liquid stream initially.

Generally, the temperature and pressure in flash vessel (3) are such as to keep the liquid stream portion molten without degrading the catalyst. Volatile material exiting flash vessel (3) through outlet (9) may be sent for recovery and recycle of aromatic hydroxy compound and optional other volatile constituents. The removal of water in flash vessel (3) may be performed under essentially isothermal conditions through supplying heat to flash vessel (3), or the removal of water in flash vessel (3) may be performed under essentially adiabatic conditions. In another embodiment the removal of water in flash vessel (3) may be performed at a temperature lower than that of the feed temperature from outlet (8) but higher than that resulting from adiabatic operation by supplying a lower amount of heat to flash vessel (3) than in the isothermal process. In various embodiments the removal of water in flash vessel (3) may be performed in one embodiment at a temperature which is greater than 30° C. higher than the temperature in the reaction vessel (1); and in another embodiment at a temperature which is at least 35° C. higher than the temperature in the reaction vessel (1). In other embodiments the removal of water in flash vessel (3) may be performed in one embodiment at a temperature which is greater than 30° C. lower than the temperature in the reaction vessel (1); and in another embodiment at a temperature which is at least 35° C. lower than the temperature in the reaction vessel (1). In one embodiment dried liquid stream from flash vessel (3) may be withdrawn through outlet (10) and separated into a stream (11) for recovery and isolation of diaryl carbonate and any catalyst constituents, and a stream (12) for recycle of dried reaction mixture to the reaction vessel (1). Optionally, at least one holding vessel, or at least one filtration device for solid removal, or both may be present between flash vessel (10) and reaction vessel (1). The ratio of stream (11) for recovery and stream (12) for recycle to reaction vessel (1) is in a range of about 0.1–30 and preferably in a range of about 0.5–15. Optionally, make-up aromatic hydroxy compound and optional other volatile constituents and make-up catalyst constituents may be added to a reaction vessel (1) or to a liquid stream at some point in the process loop before return to reaction vessel (1), or both. In one embodiment make-up aromatic hydroxy compound and optional other volatile constituents and make-up catalyst constituents are added to a dried liquid stream returning to a reaction vessel.

Figure 2:
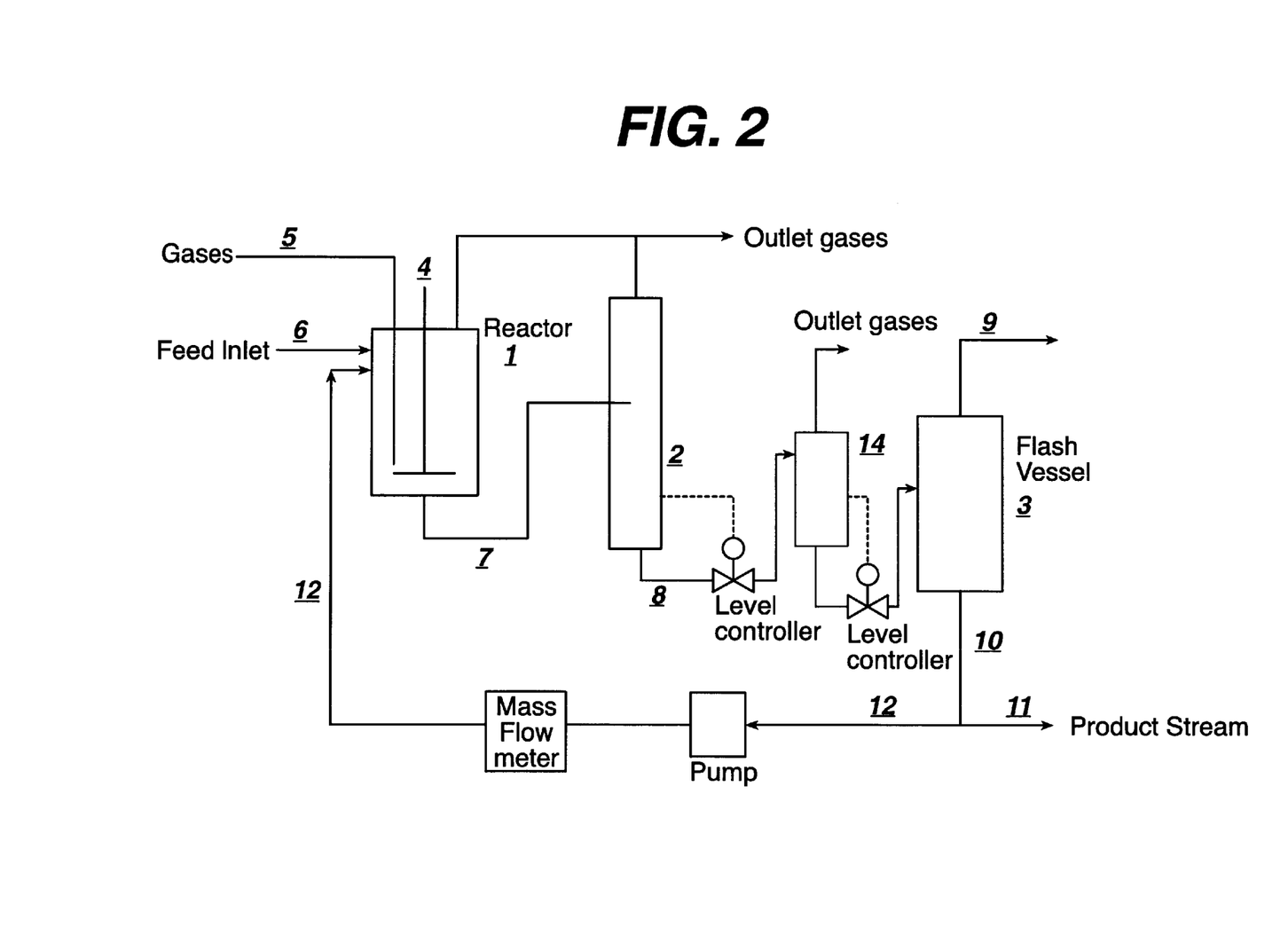
FIG. 2 is another flow diagram for a process which removes water.

In another embodiment of the invention FIG. 2 shows a flow diagram for an embodiment of the process that is essentially identical in equipment and operation to the process described in the flow diagram of FIG. 1, with the exception that a second disengagement vessel (14) is included between a first disengagement vessel (2) and flash vessel (3). The second disengagement vessel (14) is maintained at lower pressure than the first disengagement vessel. In preferred embodiments the second disengagement vessel (14) is maintained at essentially atmospheric pressure, more preferably at slightly above atmospheric pressure, and still more preferably at a pressure in a range of between about 102 and about 345 kilopascals. A liquid stream in second disengagement vessel (14) at atmospheric pressure experiences loss of dissolved gases when a liquid stream experiences the lower pressure in a second disengagement vessel (14) compared to the pressure in first disengagement vessel (2). A liquid stream from second disengagement vessel (14) is sent to flash vessel (3) through an outlet (16) and treated in the same manner as described for the process in FIG. 1. Because dissolved gases have escaped from the liquid stream in second disengagement vessel (14), less aromatic hydroxy compound is entrained and lost from flash vessel (3) when the liquid stream from (16) undergoes pressure drop in flash vessel (3). Another advantage is that less capacity from the vacuum pump attached to the evaporation unit is required, and it is easier to get to low pressures in the evaporation unit.

Dissolved gases which escape from a liquid stream through outlet (15) from second disengagement vessel (14) are recycled using standard methods. Typically outlet gases are cooled to condense and remove water and other condensable compounds before reuse of gas.

In the various embodiments of the invention the reduction of the pressure of a liquid stream taken from a reaction vessel (1) to the pressure of a flash vessel (3) may be done in either a single stage or in more than one stage. In a particular embodiment the reduction in pressure of a liquid stream may be done in two to five stages between a reaction vessel (1) and a flash vessel (3).

In a preferred embodiment water removal in the integrated process for oxidative carbonylation of aromatic hydroxy compounds is continuous. When equilibrium is attained in the process, water levels in the at least one reaction vessel are typically at essentially a constant level of about 1000–10,000 ppm, and preferably about 2000–5000 ppm. Water levels in the dried liquid stream portion exiting flash vessel (3) are typically about 50–2000 ppm, and preferably about 250–1000 ppm.

One of the advantages of embodiments of this invention is that in various embodiments there is no requirement to depressurize the gas in order to separate it from the liquid prior to the flash operation. Thus, gas recompression costs may be minimized. In addition, the water removal process described herein is more economically viable than using molecular sieves for drying reaction mixtures producing products in which water is deleterious to the process and/or products produced therefrom.

Diaryl carbonates produced by the method may be recovered and isolated at any convenient point in the process loop. In various embodiments at least a portion of diaryl carbonate is recovered from dried liquid stream. In other embodiments at least a portion of diaryl carbonate is recovered from a liquid stream before drying. In one embodiment at least a portion of diaryl carbonate is recovered from a liquid stream taken directly from a reactor and before drying. In another embodiment at least a portion of diaryl carbonate is recovered from at least a portion of a liquid stream taken directly from a reactor and before drying. In still other embodiments at least a portion of diaryl carbonate may be recovered from streams taken from at least two points in a process loop.

Embodiments of the invention are illustrated by the following non-limiting examples.

EXAMPLE 1

A reaction was run at about 10.3 megapascals at 100° C. using 15 ppm palladium as palladium acetylacetonate, 5 equivalents (versus Pd) of copper as $Cu(acac)_2$, 15 equivalents (versus Pd) of titanium as $TiO(acac)_2$, 804 equivalents (versus Pd) of tetraethylammonium bromide, 402 equivalents (versus Pd) of base (sodium hydroxide), and no molecular sieves. Gases used were a mixture of carbon monoxide (91%) and oxygen (9%). After 30 minutes the reaction was cooled to 60° C., stirring was stopped, and the reactor depressurized. The contents were removed and put into a rotary evaporator at about 60° C, where about 22 grams were evaporated. The contents were removed from the rotary evaporator, and phenol make-up was added to account for the mass removed during the rotary evaporation process, after which the contents were re-introduced into the reactor and the reaction resumed at about 10.3 megapascals and 100° C. for 30 minutes. The reactor was then cooled to 60° C. and depressurized, and the contents were put into a rotary evaporator as before, and 14 grams were evaporated, and again make-up phenol was re-added to account for the removed mass before resuming the reaction. The reaction was then permitted to run until a total of 2.05 hours of reaction had occurred. The initial total mass of reactants and catalyst (not including gases) was 99.39 grams. After 2.05 hours of reaction, there was 30.3% by weight of DPC as determined by HPLC.

Comparative Example 1A

A reaction was run at about 12.4 megapascals at 100° C. using 15 ppm palladium as palladium acetylacetonate, 5 equivalents (versus Pd) of copper as $Cu(acac)_2$, 15 equivalents (versus Pd) of titanium as $TiO(acac)_2$, 780 equivalents (versus Pd) of tetraethylammonium bromide, 400 equivalents (versus Pd) of base (sodium hydroxide), and 30 grams of molecular sieves (type 3A) to absorb water during the reaction. Gases used were a mixture of carbon monoxide (91%) and oxygen (9%). The total mass of reactants and catalyst (not including gases) was 65.83 grams. After 2.5 hours of reaction, there was 30.4% by weight of DPC as determined by HPLC.

Comparative Example 1B

A reaction was run at about 12.4 megapascals at 100° C. using 15 ppm palladium as palladium acetylacetonate, 5 equivalents (versus Pd) of copper as $Cu(acac)_2$, 15 equivalents (versus Pd) of titanium as $TiO(acac)_2$, 800 equivalents (versus Pd) of tetraethylammonium bromide, 400 equivalents (versus Pd) of base (sodium hydroxide), and no molecular sieves. Gases used were a mixture of carbon monoxide (91%) and oxygen (9%). The reaction was run until a total of 2.5 hours of reaction had occurred. The initial total mass of reactants and catalyst (not including gases) was 99.63 grams. After 1, 1.5, 2, and 2.5 hours of reaction there was 13.5%, 14.5%, 14.6%, and 14.4% by weight of DPC respectively as determined by HPLC.

Comparison of example 1 with comparative example 1B shows the improvement obtained from water removal (example 1) versus not using water removal (example 1B). Comparison of example 1 with comparative example 1A shows that the evaporative method provides comparable improvement in the reaction performance versus the molecular sieve method for water removal.

EXAMPLE 2

A reaction is run with phenol under pressure of carbon monoxide and oxygen at about 80–100° C. using a palladium source, a manganese source as inorganic co-catalyst, a tetraalkylammonium bromide, sodium hydroxide as base, and no molecular sieves. After about 30 minutes the reaction is cooled to below about 80° C., stirring is stopped, and the reactor depressurized. The reactor contents are removed and put into a rotary evaporator at about 60° C., and subjected to evaporation to remove a portion of volatile material containing a substantial amount of water than is in the reaction mixture and some unreacted phenol. The contents are removed from the rotary evaporator, and phenol make-up is added to account for the mass removed during the rotary evaporation process, after which the contents are re-introduced into the reactor and the reaction resumes under pressure and at about 80–100° C. for about 30 minutes. The reactor is then cooled to about below about 80° C. and depressurized, and the contents are put into a rotary evaporator as before, and subjected to evaporation to remove a portion of volatile material containing a substantial amount of water than is in the reaction mixture and some unreacted phenol, and again make-up phenol is re-added to account for the removed mass before resuming the reaction. The reaction is then permitted to run until a total of about 2 hours of reaction has occurred. Between about 15 and about 35% by weight of DPC is obtained as determined by HPLC.

Comparative Example 2A

A reaction is run as described for example 2, except that molecular sieves (type 3A) are present to absorb water during the reaction. After about 2 hours of reaction, there is an amount of DPC present that is similar to that obtained in example 2 as determined by HPLC.

Comparative Example 2B

A reaction is run as described for Comparative example 2A, except that no molecular sieves are present to absorb water during the reaction. After about 2 hours of reaction, there is an amount of DPC present that is less than that obtained in example 2 as determined by HPLC.

Comparison of example 2 with comparative example 2B shows the improvement obtained from water removal (example 2) versus not using water removal (example 2B). Comparison of example 2 with comparative example 2A shows that the evaporative method provides comparable improvement in the reaction performance versus the molecular sieve method for water removal.

EXAMPLE 3 and

Comparative Examples 3A and 3B

Reactions are run as in example 2 and comparative examples 2A and 2B except that a cobalt source is employed as inorganic co-catalyst. Comparison of example 3 with comparative example 3B shows an improvement in DPC yield obtained from water removal (example 3) versus not using water removal (example 3B). Comparison of example 3 with comparative example 3A shows that the evaporative method provides comparable improvement in DPC yield versus the molecular sieve method for water removal.

EXAMPLE 4 and

Comparative Examples 4A and 4B

Reactions are run as in examples 2 and comparative examples 2A and 2B except that a lead source is employed as inorganic co-catalyst. Comparison of example 4 with comparative example 4B shows an improvement in DPC yield obtained from water removal (example 4) versus not using water removal (example 4B). Comparison of example 4 with comparative example 4A shows that the evaporative method provides comparable improvement in DPC yield versus the molecular sieve method for water removal.

EXAMPLE 5 and

Comparative Examples 5A and 5B

Reactions are run as in examples 2 and comparative examples 2A and 2B except that a copper source is employed as inorganic co-catalyst. Comparison of example 5 with comparative example 5B shows an improvement in DPC yield obtained from water removal (example 5) versus not using water removal (example 5B). Comparison of example 5 with comparative example 5A shows that the evaporative method provides comparable improvement in DPC yield versus the molecular sieve method for water removal.

EXAMPLE 6 and

Comparative Examples 6A and 6B

Reactions are run as in examples 2 and comparative examples 2A and 2B except that a combination of lead source and titanium source is employed as inorganic co-catalyst. Comparison of example 6 with comparative example 6B shows an improvement in DPC yield obtained from water removal (example 6) versus not using water removal (example 6B). Comparison of example 6 with comparative example 6A shows that the evaporative method provides comparable improvement in DPC yield versus the molecular sieve method for water removal.

EXAMPLE 7 and

Comparative Examples 7A and 7B

Reactions are run as in examples 2 and comparative examples 2A and 2B except that a combination of lead source and copper source is employed as inorganic co-catalyst. Comparison of example 7 with comparative example 7B shows an improvement in DPC yield obtained from water removal (example 7) versus not using water removal (example 7B). Comparison of example 7 with comparative example 7A shows that the evaporative method provides comparable improvement in DPC yield versus the molecular sieve method for water removal.

EXAMPLE 8 and

Comparative Examples 8A and 8B

Reactions are run as in examples 2 and comparative examples 2A and 2B except that a combination of lead source and cerium source is employed as inorganic co-catalyst. Comparison of example 8 with comparative example 8B shows an improvement in DPC yield obtained from water removal (example 8 versus not using water removal (example 8B). Comparison of example 8 with comparative example 8A shows that the evaporative method provides comparable improvement in DPC yield versus the molecular sieve method for water removal.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a diaryl carbonate which comprises contacting at least one aromatic hydroxy compound with oxygen and carbon monoxide in the presence of an amount effective for carbonylation of a catalyst composition comprising the following and any reaction products thereof:
   (A) at least one Group 8, 9, or 10 metal having an atomic number of at least 44 or a compound thereof;
   (B) at least one guanidinium salt or onium salt;
   (C) at least one metal co-catalyst; and
   (D) at least one base,
   wherein reaction water is removed by a process comprising the steps of:
      (i) removing a liquid stream from an agitated oxidative carbonylation reaction mixture in a reaction vessel and transferring the stream to a first disengagement vessel which is not agitated;
      (ii) optionally, reducing the temperature of the liquid stream;
      (iii) transferring a liquid stream from the first disengagement vessel to a flash vessel wherein the liquid stream is subjected to reduced pressure, whereby a majority of the water is removed;
      (iv) returning at least a portion of a dried liquid stream to the reaction vessel; and
      (v) optionally adding at least one of make-up aromatic hydroxy compound or other volatile constituent or catalyst component to the reaction vessel or to the dried liquid stream before return to the reaction vessel,
   wherein at least a portion of diaryl carbonate is recovered from a liquid stream either before or after water removal.

2. The method according to claim 1 wherein the reaction vessel and the first disengagement vessel are at essentially the same pressure and temperature.

3. The method according to claim 1 wherein the aromatic hydroxy compound is phenol.

4. The method according to claim 1 wherein the at least one Group 8, 9, or 10 metal in component A is palladium.

5. The method according to claim 4 wherein the at least one palladium source is selected from the group consisting of palladium, palladium black, supported palladium, palladium/carbon, palladium/alumina, palladium/silica, inorganic palladium salts, palladium chloride, palladium bromide, palladium iodide, palladium sulfate, palladium nitrate, organic palladium salts, palladium acetate, palladium oxalate, palladium (II) acetylacetonate, palladium complexes, $PdCl_2(PhCN)_2$, and $PdCl_2(PPh_3)_2$.

6. The method according to claim 1 wherein the at least one guanidinium salt or onium salt of component B is at least one salt selected from the group consisting of halides, chloride, bromide, tetrafluoroborate, and hexafluorophosphate.

7. The method according to claim 6 wherein an onium salt is an ammonium salt, a phosphonium salt, or a sulfonium salt.

8. The method according to claim 6 wherein component B is at least one chloride or bromide salt.

9. The method according to claim 8 wherein-component B is an onium bromide, an ammonium bromide, a phosphonium bromide, a sulfonium bromide, a tetraalkylammonium bromide, a tetraalkylphosphonium bromide or a hexaalkylguanidinium bromide.

10. The method according to claim 8 wherein component B is an onium chloride, an ammonium chloride, a phosphonium chloride, a sulfonium chloride, a tetraalkylammonium chloride, a tetraalkylphosphonium chloride or a hexaalkylguanidinium chloride.

11. The method according to claim 1 wherein the metal co-catalyst is at least one source of lead, cerium, cobalt, copper, titanium or manganese, or mixtures thereof.

12. The method according to claim 11 wherein the metal co-catalyst is at least one manganese source.

13. The method according to claim 11 wherein the metal co-catalyst is at least one cobalt source.

14. The method according to claim 11 wherein the metal co-catalyst is at least one copper source.

15. The method according to claim 11 wherein the metal co-catalyst is at least one lead source.

16. The method according to claim 11 wherein the metal co-catalyst is at least one lead source and at least one titanium source.

17. The method according to claim 11 wherein the metal co-catalyst is at least one lead source and at least one copper source.

18. The method according to claim 11 wherein the metal co-catalyst is at least one lead source and at least one cerium source.

19. The method according to claim 1 wherein the base is at least one alkali metal hydroxide, onium hydroxide, alkali metal phenoxide, onium phenoxide, guanidinium hydroxide or guanidinium phenoxide.

20. The method according to claim 19 wherein the base is at least one alkali metal hydroxide or alkali metal phenoxide.

21. The method according to claim 20 wherein the base is at least one of sodium hydroxide or sodium phenoxide.

22. The method according to claim 1 wherein component A is present in the amount of about 1 gram-atom of metal per 800–10,000,000 moles of aromatic hydroxy compound; component B is present in the amount of about 1–2,000 moles per gram-atom of the Group 8, 9, or 10 metal of component A; component C is present in the amount of about 0.1–200 gram-atoms of total metals per gram-atom of the Group 8, 9, or 10 metal of component A; and component D is present in an amount in a range of about 0.1 to 5000 equivalents based on component A.

23. The method according to claim 1 wherein the proportion of oxygen is about 1–50 mole percent based on total oxygen and carbon monoxide.

24. The method according to claim 1 wherein the pressure is in a range of about 0.1–51 megapascals and the temperature is in a range of about 50–160° C. in the reaction vessel.

25. The method according to claim 1 wherein the temperature of the liquid stream taken from the reaction vessel is maintained at about the temperature of the reaction mixture from which the stream was taken before the liquid stream is subjected to reduced pressure.

26. The method according to claim 25 wherein the temperature is about 50–160° C.

27. The method according to claim 1 wherein the temperature of the liquid stream taken from the reaction vessel is lowered from the temperature of the initial reaction mixture before the liquid stream is subjected to reduced pressure.

28. The method according to claim 27 wherein the temperature is about 50–90° C.

29. The method according to claim 1 wherein the pressure is in a range of about 0.7–53 kilopascals and the temperature is in a range of about 50–160° C. in the flash vessel.

30. The method according to claim 29 wherein removal of water in the flash vessel is performed under essentially isothermal conditions.

31. The method according to claim 29 wherein removal of water in the flash vessel is performed under essentially adiabatic conditions.

32. The method according to claim 29 wherein removal of water in the flash vessel is performed under conditions between those of adiabatic and isothermal.

33. The method according to claim 29 wherein removal of water in the flash vessel is performed at a temperature which is greater than 30° C. higher than the temperature in the reaction vessel.

34. The method according to claim 29 wherein removal of water in the flash vessel is performed at a temperature which is greater than 30° C. lower than the temperature in the reaction vessel.

35. The method according to claim 1 which further comprises the step of transferring a liquid stream from the first disengagement vessel to a second disengagement vessel before transfer of liquid stream to the flash vessel, wherein the second disengagement vessel is at lower pressure than the first disengagement vessel.

36. The method according to claim 35 wherein the second disengagement vessel is at a pressure in a range of between about 102 and about 345 kilopascals.

37. The method according to claim 1 wherein the water content of the dried liquid stream returned from the flash vessel to the reaction vessel is about 50–2000 ppm.

38. The method according to claim 1 wherein at least a portion of diaryl carbonate is recovered from the dried liquid stream.

39. The method according to claim 1 wherein at least a portion of diaryl carbonate is recovered from a liquid stream before water removal.

40. A method for preparing diphenyl carbonate which comprises contacting phenol with oxygen and carbon monoxide in the presence of an amount effective for carbonylation of a catalyst composition comprising the following and any reaction products thereof:

(A) at least one palladium source;

(B) at least one guanidinium salt or onium salt;

(C) a metal co-catalyst selected from the group consisting of manganese, cobalt, copper, lead, titanium and cerium, and mixtures thereof; and (D) at least one base;

wherein reaction water is removed by a process comprising the steps of:

(vi) removing a liquid stream from an agitated oxidative carbonylation reaction mixture in a reaction vessel and transferring the stream to a first disengagement vessel which is not agitated;

(vii) optionally, reducing the temperature of the liquid stream;

(viii) transferring a liquid stream from the first disengagement vessel to a flash vessel wherein the liquid stream is subjected to reduced pressure, whereby a majority of the water is removed;

(ix) returning at least a portion of a dried liquid stream to the reaction vessel; and (x) optionally adding at least one of make-up aromatic hydroxy compound or other volatile constituent or catalyst component to the reaction vessel or to the dried liquid stream before return to the reaction vessel, wherein at least a portion of diaryl carbonate is recovered from a liquid stream either before or after water removal.

41. The method according to claim 40 wherein the reaction vessel and the first disengagement vessel are at essentially the same pressure and temperature.

42. The method according to claim 40 wherein the palladium source is selected from the group consisting of palladium, palladium black, supported palladium, palladium/carbon, palladium/alumina, palladium/silica, inorganic palladium salts, palladium chloride, palladium bromide, palladium iodide, palladium sulfate, palladium nitrate, organic palladium salts, palladium acetate, palladium oxalate, palladium (II) acetylacetonate, palladium complexes, $PdCl_2(PhCN)_2$, and $PdCl_2(PPh_3)_2$;

the manganese source is selected from the group consisting of manganese halides, manganese chloride, manganese nitrate, and manganese (II) acetylacetonate;

the cobalt source is selected from the group consisting of cobalt halides, cobalt chloride, cobalt bromide, cobalt nitrate, cobalt carboxylates, cobalt (II) acetate, cobalt (II) 2-ethylhexanoate; cobalt salts of β-diketones, and cobalt (II) acetylacetonate;

the copper source is selected from the group consisting of copper alkoxides, copper aryloxides; copper salts of β-diketones, and copper (II) acetylacetonate;

the lead source is selected from the group consisting of lead oxides, $PbO$, $Pb_3O_4$, $PbO_2$; lead carboxylates, lead (II) acetate, lead (II) propionate; lead (II) nitrate, lead (II) sulfate; alkoxy lead compounds, lead (II) methoxide, aryloxy lead compounds, lead (II) phenoxide; lead (II) acetylacetonate, phthalocyanine lead, and tetraethyl lead;

the titanium source is selected from the group consisting of titanium (IV) oxide acetylacetonate, titanium (IV) methoxide, titanium (IV) ethoxide, titanium (IV) butoxide, and titanium (IV) phenoxide; and the cerium source is selected from the group consisting of cerium acetate, cerium salts of β-diketones, and cerium (III) acetylacetonate.

43. The method according to claim 40 wherein component B is at least member selected from the group consisting of ammonium salts, phosphonium salts, and sulfonium salts.

44. The method according to claim 43 wherein component B is at least one tetraalkylammonium halide.

45. The method according to claim 40 wherein the base is at least one of sodium hydroxide or sodium phenoxide; or quaternary ammonium hydroxide or quaternary ammonium phenoxide.

46. The method according to claim 40 wherein the pressure is in a range of about 0.1–51 megapascals and the temperature is in a range of about 50–160° C. in the reaction vessel.

47. The method according to claim 40 wherein the temperature of the liquid stream taken from the reaction vessel is lowered from the temperature of the initial reaction mixture before the liquid stream is subjected to reduced pressure.

48. The method according to claim 40 wherein the pressure is in a range of about 0.7–53 kilopascals and the temperature is in a range of about 50–160° C. in the flash vessel.

49. The method according to claim 48 wherein removal of water in the flash vessel is performed under essentially isothermal conditions.

50. The method according to claim 48 wherein removal of water in the flash vessel is performed under essentially adiabatic conditions.

51. The method according to claim 48 wherein removal of water in the flash vessel is performed under conditions between those of adiabatic and isothermal.

52. The method according to claim 48 wherein removal of water in the flash vessel is performed at a temperature which is greater than 30° C. higher than the temperature in the reaction vessel.

53. The method according to claim 48 wherein removal of water in the flash vessel is performed at a temperature which is greater than 30° C. lower than the temperature in the reaction vessel.

54. The method according to claim 40 which further comprises the step of transferring a liquid stream from the first disengagement vessel to a second disengagement vessel before transfer of liquid stream to the flash vessel, wherein the second disengagement vessel is at a pressure in a range of between about 102 and about 345 kilopascals.

55. The method according to claim 40 wherein at least a portion of diaryl carbonate is recovered from the dried liquid stream.

56. The method according to claim 40 wherein at least a portion of diaryl carbonate is recovered from a liquid stream before water removal.

57. A method for preparing a diaryl carbonate which comprises contacting at least one aromatic hydroxy compound with oxygen and carbon monoxide in the presence of an amount effective for carbonylation of a catalyst composition comprising the following and any reaction products thereof:

(A) at least one Group 8, 9, or 10 metal having an atomic number of at least 44 or a compound thereof;

(B) at least one guanidinium salt or onium salt;

(C) a metal co-catalyst comprising at least one copper source and at least one titanium source; and (D) at least one base, wherein reaction water is removed by a process comprising the steps of:

(i) removing a liquid stream from an agitated oxidative carbonylation reaction mixture in a reaction vessel and transferring the stream to a first disengagement vessel which is not agitated;

(ii) optionally, reducing the temperature of the liquid stream;

(iii) transferring a liquid stream from the first disengagement vessel to a flash vessel wherein the liquid stream is subjected to reduced pressure, whereby a majority of the water is removed;

(iv) returning at least a portion of a dried liquid stream to the reaction vessel; and (v) optionally adding at least one of make-up aromatic hydroxy compound or other volatile constituent or catalyst component to the reaction vessel or to the dried liquid stream before return to the reaction vessel, wherein at least a portion of diaryl carbonate is recovered from a liquid stream either before or after water removal.

58. The method according to claim 57 wherein the reaction vessel and the first disengagement vessel are at essentially the same pressure and temperature.

59. The method according to claim 57 wherein the aromatic hydroxy compound is phenol.

60. The method according to claim 57 wherein the at least one Group 8, 9, or 10 metal in component A is palladium.

61. The method according to claim 60 wherein the at least one palladium source is selected from the group consisting of palladium, palladium black, supported palladium, palladium/carbon, palladium/alumina, palladium/silica, inorganic palladium salts, palladium chloride, palladium bromide, palladium iodide, palladium sulfate, palladium nitrate, organic palladium salts, palladium acetate, palladium oxalate, palladium (II) acetylacetonate, palladium complexes, $PdCl_2(PhCN)_2$, and $PdCl_2(PPh_3)_2$.

62. The method according to claim 57 wherein the at least one guanidinium salt or onium salt of component B is at least one salt selected from the group consisting of halides, chloride, bromide, tetrafluoroborate, and hexafluorophosphate.

63. The method according to claim 62 wherein an onium salt is an ammonium salt, a phosphonium salt, or a sulfonium salt.

64. The method according to claim 62 wherein component B is at least one chloride or bromide salt.

65. The method according to claim 64 wherein component B is an onium bromide, an ammonium bromide, a phosphonium bromide, a sulfonium bromide, a tetraalkylammonium bromide, a tetraalkylphosphonium bromide or a hexaalkylguanidinium bromide.

66. The method according to claim 64 wherein component B is an onium chloride, an ammonium chloride, a phosphonium chloride, a sulfonium chloride, a tetraalkylammonium chloride, a tetraalkylphosphonium chloride or a hexaalkylguanidinium chloride.

67. The method according to claim 57 wherein component C is a mixture of: at least one titanium source selected from the group consisting of titanium alkoxides, titanium aryloxides, titanium (IV) methoxide, titanium (IV) ethoxide, titanium (IV) isopropoxide, titanium (IV) 2-ethylhexoxide, titanium(IV) butoxide, titanium (IV) 2-ethyl-1,3-hexanediolate, titanium(IV) phenoxide; titanium salts of β-diketones, titanium salts of β-ketoesters, titanium (IV) diisopropoxide bis(acetylacetonate), titanium (IV) bis(ethyl acetoacetato) diisopropoxide, and titanium (IV) oxide acetylacetonate); and at least one copper source selected from the group consisting of copper alkoxides, copper aryloxides; copper salts of β-diketones, and copper (II) acetylacetonate).

68. The method according to claim 57 wherein the base is at least one alkali metal hydroxide, onium hydroxide, alkali metal phenoxide, onium phenoxide, guanidinium hydroxide or guanidinium phenoxide.

69. The method according to claim 68 wherein the base is at least one alkali metal hydroxide or alkali metal phenoxide.

70. The method according to claim 69 wherein the base is at least one of sodium hydroxide or sodium phenoxide.

71. The method according to claim 57 wherein component A is present in the amount of about 1 gram-atom of metal per 800–1,000,000 moles of aromatic hydroxy compound; component B is present in the amount of about 1–2,000 moles per gram-atom of the Group 8, 9, or 10 metal of component A; component C is present in the amount of about 0.1–200 gram-atoms of total metals per gram-atom of the Group 8, 9, or 10 metal of component A; and component D is present in an amount in a range of about 0.1 to 5000 equivalents based on component A.

72. The method according to claim 57 wherein the proportion of oxygen is about 1–50 mole percent based on total oxygen and carbon monoxide.

73. The method according to claim 57 wherein the pressure is in a range of about 0.1–51 megapascals and the temperature is in a range of about 50–160° C. in the reaction vessel.

74. The method according to claim 57 wherein the temperature of the liquid stream taken from the reaction vessel is maintained at about the temperature of the reaction mixture from which the stream was taken before the liquid stream is subjected to reduced pressure.

75. The method according to claim 74 wherein the temperature is about 50–160° C.

76. The method according to claim 57 wherein the temperature of the liquid stream taken from the reaction vessel is lowered from the temperature of the initial reaction mixture before the liquid stream is subjected to reduced pressure.

77. The method according to claim 76 wherein the temperature is about 50–90° C.

78. The method according to claim 57 wherein the pressure is in a range of about 0.7–53 kilopascals and the temperature is in a range of about 50–160° C. in the flash vessel.

79. The method according to claim 78 wherein removal of water in the flash vessel is performed under essentially isothermal conditions.

80. The method according to claim 78 wherein removal of water in the flash vessel is performed under essentially adiabatic conditions.

81. The method according to claim 78 wherein removal of water in the flash vessel is performed under conditions between those of adiabatic and isothermal.

82. The method according to claim 78 wherein removal of water in the flash vessel is performed at a temperature which is greater than 30° C. higher than the temperature in the reaction vessel.

83. The method according to claim 78 wherein removal of water in the flash vessel is performed at a temperature which is greater than 30° C. lower than the temperature in the reaction vessel.

84. The method according to claim 57 which further comprises the step of transferring a liquid stream from the first disengagement vessel to a second disengagement vessel before transfer of liquid stream to the flash vessel, wherein the second disengagement vessel is at lower pressure than the first disengagement vessel.

85. The method according to claim 84 wherein the second disengagement vessel is at a pressure in a range of between about 102 and about 345 kilopascals.

86. The method according to claim 57 wherein the water content of the dried liquid stream returned from the flash vessel to the reaction vessel is about 50–2000 ppm.

87. The method according to claim 57 wherein at least a portion of diaryl carbonate is recovered from the dried liquid stream.

88. The method according to claim 57 wherein at least a portion of diaryl carbonate is recovered from a liquid stream before water removal.

89. A method for preparing diphenyl carbonate which comprises contacting phenol with oxygen and carbon monoxide in the presence of an amount effective for carbonylation of a catalyst composition comprising the following and any reaction products thereof:

(A) at least one palladium source;

(B) at least one guanidinium salt or onium salt;

(C) a metal co-catalyst comprising at least one copper source and at least one titanium source; and (D) at least one base;

wherein reaction water is removed by a process comprising the steps of:
(vi) removing a liquid stream from an agitated oxidative carbonylation reaction mixture in a reaction vessel and transferring the stream to a first disengagement vessel which is not agitated;
(vii) optionally, reducing the temperature of the liquid stream;
(viii) transferring a liquid stream from the first disengagement vessel to a flash vessel wherein the liquid stream is subjected to reduced pressure, whereby a majority of the water is removed;
(ix) returning at least a portion of a dried liquid stream to the reaction vessel; and
(x) optionally adding at least one of make-up aromatic hydroxy compound or other volatile constituent or catalyst component to the reaction vessel or to the dried liquid stream before return to the reaction vessel,
wherein at least a portion of diaryl carbonate is recovered from a liquid stream either before or after water removal.

90. The method according to claim 89 wherein the reaction vessel and the first disengagement vessel are at essentially the same pressure and temperature.

91. The method according to claim 89 wherein the palladium source is selected from the group consisting of palladium, palladium black, supported palladium, palladium/carbon, palladium/alumina, palladium/silica, inorganic palladium salts, palladium chloride, palladium bromide, palladium iodide, palladium sulfate, palladium nitrate, organic palladium salts, palladium acetate, palladium oxalate, palladium (II) acetylacetonate, palladium complexes, $PdCl_2(PhCN)_2$, and $PdCl_2(PPh_3)_2$;

the copper source is selected from the group consisting of copper alkoxides, copper aryloxides; copper salts of β-diketones, and copper (II) acetylacetonate); and the titanium source is selected from the group consisting of titanium (IV) oxide acetylacetonate, titanium (IV) methoxide, titanium (IV) ethoxide, titanium (IV) butoxide, titanium (IV) phenoxide.

92. The method according to claim 89 wherein component B is at least member selected from the group consisting of ammonium salts, phosphonium salts, and sulfonium salts.

93. The method according to claim 89 wherein component B is at least one tetraalkylammonium halide.

94. The method according to claim 89 wherein the base is at least one of sodium hydroxide or sodium phenoxide; or quaternary ammonium hydroxide or quaternary ammonium phenoxide.

95. The method according to claim 89 wherein the pressure is in a range of about 0.1–51 megapascals and the temperature is in a range of about 50–160° C. in the reaction vessel.

96. The method according to claim 89 wherein the temperature of the liquid stream taken from the reaction vessel is lowered from the temperature of the initial reaction mixture before the liquid stream is subjected to reduced pressure.

97. The method according to claim 89 wherein the pressure is in a range of about 0.7–53 kilopascals and the temperature is in a range of about 50–160° C. in the flash vessel.

98. The method according to claim 97 wherein removal of water in the flash vessel is performed under essentially isothermal conditions.

99. The method according to claim 97 wherein removal of water in the flash vessel is performed under essentially adiabatic conditions.

100. The method according to claim 97 wherein removal of water in the flash vessel is performed under conditions between those of adiabatic and isothermal.

101. The method according to claim 97 wherein removal of water in the flash vessel is performed at a temperature which is greater than 30° C. higher than the temperature in the reaction vessel.

102. The method according to claim 97 wherein removal of water in the flash vessel is performed at a temperature which is greater than 30° C. lower than the temperature in the reaction vessel.

103. The method according to claim 89 which further comprises the step of transferring a liquid stream from the first disengagement vessel to a second disengagement vessel before transfer of liquid stream to the flash vessel, wherein the second disengagement vessel is at a pressure in a range of between about 102 and about 345 kilopascals.

104. The method according to claim 89 wherein at least a portion of diaryl carbonate is recovered from the dried liquid stream.

105. The method according to claim 89 wherein at least a portion of diaryl carbonate is recovered from a liquid stream before water removal.

* * * * *